United States Patent [19]

Maillard

[11] Patent Number: 4,791,939
[45] Date of Patent: Dec. 20, 1988

[54] STYLET FOR USE WITH AN IMPLANTABLE PACING LEAD

[75] Inventor: Germain Maillard, La Chaux-de-Fonds, France

[73] Assignee: Nivarox-FAR S.A., Le Locle, Switzerland

[21] Appl. No.: 878,540

[22] Filed: Jun. 25, 1986

[30] Foreign Application Priority Data

Jun. 27, 1985 [FR] France ................................. 85 09986

[51] Int. Cl.$^4$ ............................................. A61N 1/00
[52] U.S. Cl. .................................. 128/786; 128/419 P; 128/772
[58] Field of Search ..................... 128/419 P, 784, 785, 128/786, 748, 642, 341, 657, 737, 772, 303 R

[56] References Cited

U.S. PATENT DOCUMENTS

| | | | |
|---|---|---|---|
| 1,730,993 | 1/1928 | Buchanan et al. | 254/134.3 FT |
| 2,118,631 | 5/1938 | Wappler | 128/657 |
| 2,816,552 | 12/1957 | Hoffman | 128/341 |
| 2,980,398 | 4/1961 | Raney et al. | 254/134.3 FT |
| 3,999,551 | 12/1976 | Spitz et al. | 128/303 R |
| 4,169,479 | 10/1979 | Muto | 128/419 P |
| 4,498,482 | 2/1985 | Williams | 128/786 |
| 4,564,023 | 1/1986 | Hess | 128/785 |
| 4,676,249 | 6/1987 | Arenas et al. | 128/657 |

FOREIGN PATENT DOCUMENTS

| | | | |
|---|---|---|---|
| 1435797 | 10/1973 | United Kingdom | 128/657 |
| 2064963 | 6/1981 | United Kingdom . | |

Primary Examiner—Francis J. Jaworski
Assistant Examiner—Manuel George
Attorney, Agent, or Firm—Sughrue, Mion, Zinn, Macpeak, and Seas

[57] ABSTRACT

A stylet for use with an implantable pacing lead and for checking purposes after this implantation. The pacing lead is a hollow elongated conductor including coiled wire forming continuous turns. The stylet comprises a flexible, straight filament and a blunting tip having an axially symmetrical shape. The rear end of the tip is provided with an axially symmetrical cavity at the bottom of which is secured the distal end of the filament. Upon insertion of the stylet in the conductor of an implanted pacing lead, for example for checking the correct connection of the conductor in the heart's tissue, the tip by virtue of its shape is prevented from catching in the grooves, existing between the turns of the coiled wire, as the style moves around bends formed in the conductor while it is in a blood vessel, thereby facilitating the insertion of the stylet.

10 Claims, 2 Drawing Sheets

STYLET FOR USE WITH AN IMPLANTABLE PACING LEAD

BACKGROUND OF THE INVENTION

This invention relates to pacing leads that are implantable in the body and is more particularly concerned with a stylet for use with such pacing leads with a view to stiffening them during implantation.

Implantable pacing leads are nowadays widely used in medicine for making diagnoses, for treating patients and particularly for providing cardiacs with pacemakers.

These pacing leads comprise a hollow elongated electric conductor that is highly flexible and which is sheathed with insulating material over its entire length. The conductor as such usually consists of a helical winding of several strands of wire, the strands being also helicoidally wound. Such a construction provides the conductor with the required flexibility for it continuously to adapt to the changes in shape of the blood vessels through which it extends, in particular in the region of the heart. For implantation, however, the conductor should be sufficiently rigid for the pacing lead to be inserted in the blood vessels and it is one of the functions of a stylet temporarily to provide the conductor with the required stiffness. Such a stylet may comprise a stiffish filament of elastic metal that is inserted into the pacing lead conductor and that is somewhat longer than the latter.

Once the assembly of the pacing lead and the stylet is implanted by a surgeon, he then withdraws the latter and connects the distal end of the pacing lead conductor to a pacemaker or similar device.

As is known, a pacing lead, particularly a pacing lead used to pace the heart, must become fastened to the tissue having to be stimulated and this is generally achieved by providing the operative member or electrode of the pacing lead with a suitably shaped head for example by means of a particular configuration of its surface or by barbs inclined to the longitudinal axis of the pacing lead. Despite these precautions, the pacing electrode still frequently comes loose, particularly during the first few weeks after implantation as the tissue has not yet been able to grow sufficiently to latch on to the electrode to keep the pacing lead in place. Surgeons thus regularly check whether the pacing lead has fastened properly some time after implanting it. This checking operation may be performed with a stylet similar to that used for the implantation.

An implanted pacing lead normally closely follows the sinuosities of the blood vessels in which it is inserted. At time, however, it may become quite convoluted after the stylet is withdrawn, particularly where the blood vessel branches off. The conductor of the pacing lead may then, for instance, form single or even double, e.g. S-shaped, twists or bends. Now, if the stylet filament is fitted with a simple blunting tip such as a ball point (such as disclosed in UK Patent Application No 2, 064, 963) or even more simply is formed with a rounded nose (such as dislosed in U.S. Pat. No. 2,118,631), the stylet can then only be inserted with difficulty into the conductor as the tip or nose tends to catch in the grooves between the contiguous turns of the conductor. In so doing, the tip or nose will tend to move them apart and even to be pushed through the conductor and the insulating sheath surrounding it. If this happens, the stylet is then very likely to perforate the blood vessel. This has induced practitioners to discard this method of checking the implantation of pacing leads and to resort to X-rays instead.

SUMMARY OF THE INVENTION

An object of the invention is to provide a stylet with which an implantation can be checked without danger of piercing the conductor of the pacing lead or the blood vessel.

The invention thus provides a stylet that can be used both to implant an implantable pacing lead and to check an implanted pacing lead of the kind having a hollow elongated conductor of coiled wire forming contiguous turns, said stylet comprising a stiffish elastic filament insertable in said conductor and a blunting tip having an axially-symmetrical bullet shape and having a diameter less than the internal diameter of said conductor, said tip being secured to the distal of the filament.

With such a design, the blunting tip cannot catch in the grooves between the contiguous turns of the conductor, even if the latter forms tight bends. This is because when the elastic filament is being pushed inwardly and the tip encounters resistance from the contiguous conductor turns in the bends, the filament is caused to flex thereby causing the tip to tilt and its nose to move away from the turns of the conductor, with the result that the tip is caused to slip along its side over the conductor turns in the bends, hence considerably facilitating insertion of the stylet during a checking operation.

The tilting action on the tip can be enhanced and the insertion of the stylet facilitated still further if the tip is formed at its rear end with an axial, generally cylindrical, recess into which extends the distal end portion of the filament, the distal end of the filament being secured to the tip at a region proximate to the bottom of the recess, the latter having a diameter substantially greater than that of the distal end of the filament in the recess.

The forces involved in the tilting action can thus be made to act on the tip at points that are as far apart as possible from each other. With such a construction for the tip, even tighter bends can be negotiated without danger of piercing the conductor or a blood vessel.

BRIEF DESCRIPTION OF THE DRAWINGS

In the accompanying drawings, given by way of example.

DETAILED DESCRIPTION

Figure 1:
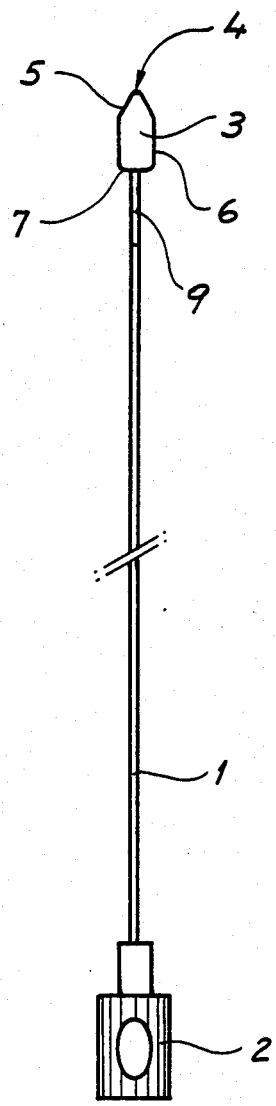
FIG. 1 illustrates on an enlarged scale a stylet according to the invention.

The stylet shown in FIG. 1 comprises a stiffish elastic filament 1, a manipulation knob 2 secured to the proximal (here bottom) end of filament 1 and a generally bullet-shaped blunting tip 3 secured to the distal (here top) end of filament 1 which may taper slightly at 9 adjacent tip 3.

Tip 3 has, on the outside, a rounded nose 4, a frusto-conical surface 5 which smoothly merges at its narrow end with nose 4, and a rear cylindrical surface 6 which smoothly merges with the broad end of surface 5.

Knob 2 and tip 3 are secured to filament 1 as by brazing or by setting the opposite ends of filament 1 in the body of knob 2 and of tip 3.

The entire stylet may for instance be made of stainless steel.

As a matter of example only, the diameter of tip 3 is of at most 0,60 mm when the internal diameter of the conductor (not shown in FIG. 1) of an implantable pacing lead associated with the stylet is of 0,80 mm. The length of the tip is of about 1,20 mm, while the cylindrical part of filament 1 should have a diameter of about 0,20 mm.

In the embodiment of FIG. 1, tip 3 is solid and filament 1 is only free from the rear end face 7 of tip 3.

Figure 2:
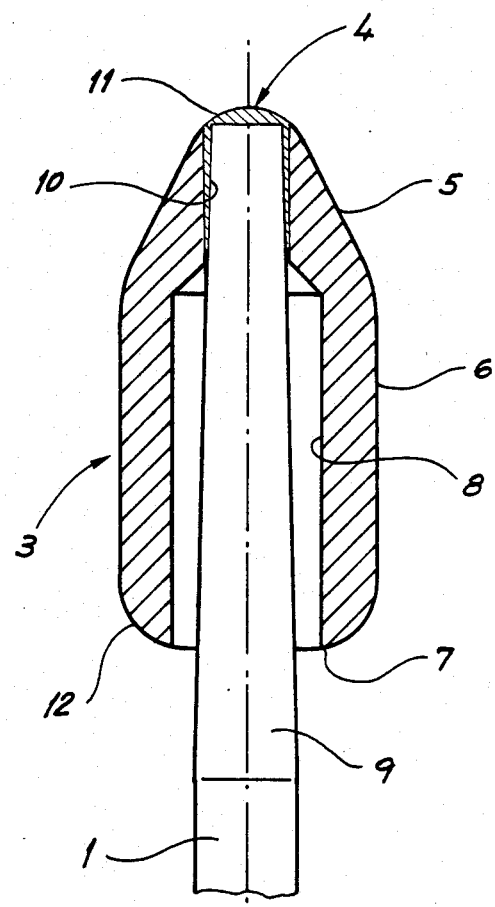
FIG. 2 shows, partly in axial section, a modified, preferred, constructional form for the distal (here upper) end portion of the stylet shown in FIG. 1.

In the embodiment of FIG. 2, tip 3 is formed with an axial, generally cylindrical recess 8 at its rear end 7 and with an axial, cylindrical aperture 10 of lesser diameter extending from the bottom of recess 8 to the front end of tip 3. It may be noted that the diameter of recess 8 is significantly higher than the diameter of filament 1. For example if the diameter of filament 1 is of 0,20 mm, the recess should have a diameter of about 0,35 mm.

The distal end portion 9 of filament 1 tapers slightly, and extends through recess 8 into aperture 10 in which it is secured by solder 11. Solder 11 is shaped to from on tip 3 a nose 4 that is rounded to merge smoothly with the adjoining narrow end of frusto-conical surface 5.

Alternatively, filament portion 9 may be secured by projecting its end slightly beyond aperture 10 and spreading it to rivet portion 9 to tip 3 and to provide nose 4.

By slightly tapering portion 9 and suitably sizing aperture 10, filament 1 can be arranged firstly to position itself automatically axially in relation to tip 3 through portion 9 by wedging itself in aperture 10 and secondly to project out of aperture 10, whereupon the projecting end of filament 1 can be cut off as required for a soldering or riveting operation.

It has been found that the slant of frusto-conical surface 5 with respect to the axis of tip 3 must be carefully choosen. According to the expected curvature of the pacing lead when implanted in the body, the slant angle can be choosen between 15° and 50°. However it has been found that an angle of 26° as best suited to the usual curvature conditions encountered in practice.

Advantageously, a rounded surface portion 12 is formed at the rear end of tip 3 to facilitate withdrawal of the stylet from the pacing lead either after implantation or after checking of the latter.

Figure 3:
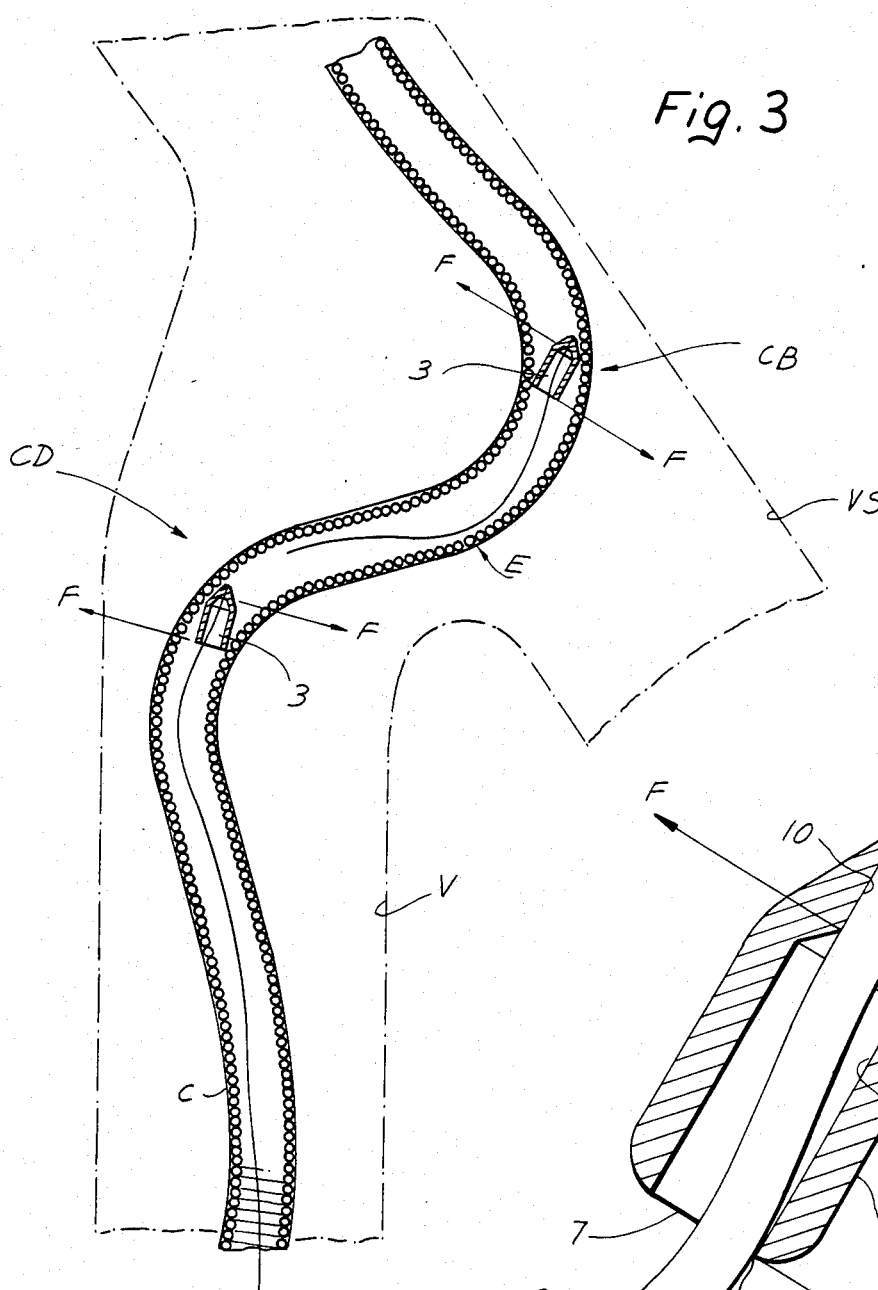
FIG. 3 diagrammatically illustrates the progress of the insertable portion of a stylet as modified in FIG. 2, inside a hollow conductor, following a sinuous path, of an implanted pacing lead.

FIG. 3 shows the operation of a stylet according to the embodiment of FIG. 2. A blood vessel V has been provided with a conductor E of an implantable pacing lead. Conductor E consists of a hollow helicoidal winding C of several strands of thin electrically conductive wires also helicoidally wound, the conductor being provided with an insulating sheath over its entire length. A secondary blood vessel VS is shown branching off vessel V and it is assumed that a few days after implantation, conductor E has formed in the region of the branching off point a first sharp bend CD to the right followed by a sharp bend CB to the left as viewed from the proximal end of the pacing lead (at the lower part of FIG. 3).

When the described and illustrated stylets are not being acted upon in any way, they are normally quite straight as shown in FIG. 1 and they will tend to return to this configuration when released after having been moved away therefrom. But their filaments 1 while having to be quite stiff, nevertheless should be sufficiently flexible to follow the bends of blood vessel V as the pacing lead is being implanted or to travel round bends in a conductor E during a subsequent insertion operation.

FIG. 3 illustrates what happens during a subsequent insertion operation. As tip 3 enters bend CD it comes into contact with the inner surface of conductor E and its progression is arrested by a turn thereof.

With prior art stylets involving a blunting tip consisting merely of a small ball point or a rounded nose, the inner surface of conductor E will offer substantial resistance in a bend due to the presence of helical grooves between the contiguous turns of the several strands of conductor E, thereby inhibiting further progress of the tip.

With the tips described and illustrated, on the other hand, as soon as filament 1 becomes subjected to slight axial strain due to the resistance exerted on tip 3 by the inner surface on conductor E and the force applied to knob 2 by a surgeon, it flexes slightly in the region of tip 3 thereby causing tip 3 to tilt out of alignment with filament portion 9. This causes frustoconical surface 5 of tip 3 instead of nose 4 to come into contact with the inner surface of conductor E. Because of the slant of surface 5, the latter is able to ride on, and not to catch in, the groove (s) formed between the successive turns of conductor E. This tilting action of tip 3 will occur whenever it encounters sufficient resistance to cause portion 9 to flex and whenever this resistance drops, portion 9 will straighten causing tip 3 to resume its normal position as shown in FIG. 2.

Figure 4:
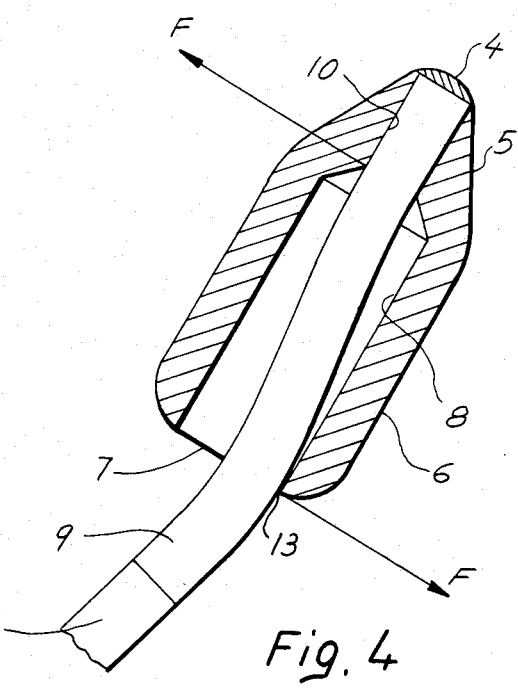
FIG. 4 shows, partly in section and on an enlarged scale, the distal end portion of the stylet visible in FIG. 3.

The forces involved in the tilting action of tip 3 are identified as F—F in FIG. 4. The moment of the resulting couple tends to move tip 3 away from the resisting surface or at least to apply thereagainst a generatrix of tip surface 5.

Because of the tip's axially symmetrical shape, the above couple may occur in any axial plane of tip 3 as determined by the flexing plane of portion 9, which may be in the plane of FIG. 3 or any other plane.

The tilting action described above will occur both with the tip described with reference to FIG. 1 and with the tip illustrated in FIGS. 2 and 4. The latter construction will, however, produce a couple having a much greater moment since the force acting nearest tip 3 is made to act as closely as possible to the front end of tip 3, and if filament portion 9 flexes sufficiently to contact the rear end of tip 3 at 13 (FIG. 4), the tilting action is enhanced still further.

I claim:

1. For use with an implantable pacing lead of the type having a hollow elongated conductor of coiled wire forming continuous turns, a stylet, removably insertable in said hollow conductor, and comprising:
    a flexible, straight filament having a proximal end and a distal end;
    a blunting tip secured at the distal end of said filament; and
    a manipulation knob secured at the proximal end of said filament; and wherein:

said tip has an ogival shape which is symmetrical about a longitudinal axis of the tip from a front end to a rear end of the tip;

the tip is provided with a cavity which is symmetrical about said longitudinal axis and which has a front portion, in an area proximate to the front end of said tip, and a rear portion extending from said front portion to said rear end of said tip, said rear portion having a cross-section, taken in a plane perpendicular to said longitudinal axis, larger than a cross-section, taken in a plane perpendicular to said longitudinal axis, of said front portion, and the cross-section of said front portion of said cavity corresponding to a cross-section, taken in a plane perpendicular to said longitudinal axis, of said distal end of said filament, said distal end of said filament being secured in said front portion of said cavity; and the shape of said tip comprises, from the front end to the rear end: a rounded nose portion; a frusto-conical portion having a narrow front end, which smoothly emerges with said nose portion, and a broader rear end.

2. A stylet according to claim 1, wherein said filament comprises a front end portion that tapers towards the distal end of the filament.

3. A stylet according to claim 1, wherein the shape of said tip further comprises a rear cylindrical surface portion which smoothly merges with the broader end of said frusto-conical surface portion.

4. A stylet as in claim 3, wherein said frusto-conical surface portion is inclined to the axis of said tip by an angle ranging from 15° to 50°.

5. A stylet as in claim 4, wherein said angle is about 26°.

6. In an implantable pacing lead assembly of the type having (1) a pacing lead in the form of a hollow elongated conductor of coiled wire forming continuous turns and (2) a stylet, removably insertable in said hollow conductor, the improvement wherein said stylet comprises:

a flexible, straight filament having a proximal end and a distal end;

a blunting tip secured at the distal end of said filament; and a manipulation knob secured at the proximal end of said filament; and wherein:

said tip has an ogival shape which is symmetrical about a longitudinal axis of the tip from a front end to a rear end of the tip;

the tip is provided with a cavity which is symmetrical about said longitudinal axis and which has a front portion, in an area proximate to the front end of said tip, and a rear portion extending from said front portion to said rear end of said tip, said rear portion having a cross-section, taken in a plane perpendicular to said longitudinal axis, larger than a cross-section, taken in a plane perpendicular to said longitudinal axis, of said front portion, and the cross-section of said front portion of said cavity corresponding to a cross-section, taken in a plane perpendicular to said longitudinal axis, of said distal end of said filament, said distal end of said filament being secured in said front portion of said cavity; and the shape of said tip comprises, from the front end to the rear end: a rounded nose portion; a frusto-conical portion having a narrow front end, which smoothly emerges with said nose portion, and a broader rear end.

7. An implantable pacing lead assembly according to claim 6, wherein said filament comprises a front end portion that tapers towards the distal end of the filament.

8. An implantable pacing lead assembly according to claim 6, wherein the shape of said tip further comprises a rear cylindrical surface portion which smoothly merges with the broader end of said frusto-conical surface portion.

9. An implantable pacing lead assembly according to claim 8, wherein said frusto-conical surface portion is inclined to the axis of said tip by an angle ranging from 15° to 50°.

10. An implantable pacing lead assembly according to claim 9, wherein said angle is about 26°.

* * * * *